(12) United States Patent
Flusberg et al.

(10) Patent No.: US 9,411,149 B2
(45) Date of Patent: Aug. 9, 2016

(54) MICROENDOSCOPY WITH CORRECTIVE OPTICS

(75) Inventors: Benjamin A. Flusberg, Palo Alto, CA (US); Mark Jacob Schnitzer, Stanford, CA (US); Tony H. Ko, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 2450 days.

(21) Appl. No.: 12/175,234

(22) Filed: Jul. 17, 2008

(65) Prior Publication Data

US 2009/0054791 A1 Feb. 26, 2009

Related U.S. Application Data

(60) Provisional application No. 60/950,232, filed on Jul. 17, 2007.

(51) Int. Cl.
| | | |
|---|---|---|
| *A61B 6/00* | (2006.01) | |
| *G02B 23/24* | (2006.01) | |
| *A61B 5/00* | (2006.01) | |
| *G02B 3/00* | (2006.01) | |
| *G02B 27/00* | (2006.01) | |

(52) U.S. Cl.
CPC .......... *G02B 23/2423* (2013.01); *A61B 5/0059* (2013.01); *G02B 3/0087* (2013.01); *G02B 27/0025* (2013.01)

(58) Field of Classification Search
CPC ............................ A61B 5/0059; A61B 5/0084
USPC ........................................................ 600/476
See application file for complete search history.

(56) References Cited

U.S. PATENT DOCUMENTS

| | | | |
|---|---|---|---|
| 5,161,063 A | | 11/1992 | Krill et al. |
| 6,057,968 A | * | 5/2000 | Konishi et al. ................ 359/654 |
| 6,166,385 A | | 12/2000 | Webb et al. |
| 6,301,043 B1 | * | 10/2001 | Lei ................................ 359/435 |
| 6,344,653 B1 | | 2/2002 | Webb et al. |
| 6,643,071 B2 | | 11/2003 | Schnitzer |
| 7,091,500 B2 | | 8/2006 | Schnitzer |
| 2001/0029316 A1 | | 10/2001 | Webb |
| 2002/0141714 A1 | * | 10/2002 | Reed et al. .................... 385/116 |
| 2002/0146202 A1 | | 10/2002 | Reed et al. |
| 2003/0031410 A1 | | 2/2003 | Schnitzer |
| 2003/0117715 A1 | * | 6/2003 | Schnitzer ..................... 359/652 |
| 2003/0118305 A1 | | 6/2003 | Reed et al. |

(Continued)

OTHER PUBLICATIONS

Monfared et al. "In Vivo Imaging of Mammalian Cochlear Blood Flow Using Fluorescence Microendoscopy." Otology & Neurology 27(2):144-152 (2006).
Flusberg et al. "In vivo brain imaging using a portable 3.9 gram two-photon fluorescence microendoscope." Optics Letters 30(17): 2272-2274 (Sep. 1, 2005).

(Continued)

*Primary Examiner* — Tse Chen
*Assistant Examiner* — Hien Nguyen
(74) *Attorney, Agent, or Firm* — Crawford Maunu PLLC (57) ABSTRACT

Micro-optical imaging is facilitated. According to an example embodiment, a micro-optical probe arrangement includes a GRIN-type lens probe to direct light to and from a specimen. Compensation optics tailored to the probe and aberrations introduced by the lens are located in a light path through the lens, and compensate for the introduced aberrations. A light detector detects light from the specimen, as facilitated by the compensation optics, and generates data characterizing an image of the specimen.

9 Claims, 6 Drawing Sheets

(56) References Cited

U.S. PATENT DOCUMENTS

| | | |
|---|---|---|
| 2003/0174409 A1* | 9/2003 | Nagaoka .................... 359/654 |
| 2003/0191397 A1 | 10/2003 | Webb |
| 2004/0143190 A1 | 7/2004 | Schnitzer |
| 2004/0260148 A1 | 12/2004 | Schnitzer |
| 2005/0137075 A1 | 6/2005 | Messerschmidt et al. |

OTHER PUBLICATIONS

Engelbrecht et al. "Ultra-compact fiber-optic two-photon microscope for functional fluorescence imaging in vivo." Optics Express 16(8): 5556-5564 (Apr. 4, 2008).

U.S. Appl. No. 11/338,598, filed Jan. 24, 2006, Flusberg et al.

U.S. Appl. No. 11/334,769, filed Jan. 18, 2006, Schnitzer et al.

\* cited by examiner

MICROENDOSCOPY WITH CORRECTIVE OPTICS

RELATED PATENT DOCUMENTS

This patent document claims the benefit, under 35 U.S.C. §119(e), of U.S. Provisional Patent Application Ser. No. 60/950,232, entitled Grin-Lens Microendoscopy with Corrective Optics and filed on Jul. 17, 2007; this patent application is fully incorporated herein by reference.

FEDERALLY-SPONSORED RESEARCH OR DEVELOPMENT

This invention was made with Government support under contract NS050533 awarded by the National Institutes of Health. The Government has certain rights in this invention.

FIELD OF THE INVENTION

The present invention relates generally to imaging, and more specifically to imaging specimen using micro-optics devices.

BACKGROUND

In recent years, a variety of approaches to optical imaging have been used for many different applications. For example, microscopes and related probes have been extensively used for research, testing and treatment of diseases or other illnesses. For invasive applications, endoscopes or other probes have been used for imaging specimen, such as for imaging tissue in anesthetized animals. For these and related applications, advancements have been made in developing relatively less-invasive imaging approaches in terms of optical components and other related equipment in order to facilitate access to tissue under one or more of a variety of conditions.

One type of optical component that has been used in applications benefiting from relatively small size is the gradient-refractive index (GRIN) lens. GRIN lenses have been used in a variety of applications, such as for imaging in photocopiers and scanners, and for microscopy and endoscopy applications. GRIN lenses are often implemented with glass rods that have a refractive index profile that is a function of the radius (or axial position) within the glass. This refractive index profile serves to focus light. For microscopy and endoscopy applications, GRIN lenses often range in diameter from a few millimeters to a few hundred microns.

Many GRIN lenses suffer from optical aberrations in one or both of the axial and lateral dimensions. These aberrations may include, for example, chromatic, spherical, astigmatism, coma, field curvature and distortion aberration. These aberrations tend to degrade the optical resolving power of GRIN lenses and prevent them from having diffraction-limited point spread functions (PSF). For example, the PSF of a 1-mm diameter doublet GRIN lens system may be in a range of about 0.9-1.2 microns in the lateral dimension, which is about 2-2.5 times the diffraction limit. For some applications, these aberrations and related characteristics are not significant or otherwise do not present issues with respect to imaging. However, GRIN lenses have been challenging to implement for a variety of applications in which such aberrations hinder the ability to form desired images, such as for fluorescence microendoscopy. Adequate resolution is often unattainable for a variety of applications needing or benefiting from a relatively high numerical aperture (NA), such as for imaging dendritic spines and mitochondria.

Difficulties associated with the above have presented challenges to imaging applications, including those involving the implementation of such micro-lens optics.

SUMMARY

The present invention is directed to overcoming the above-mentioned challenges and others related to imaging devices and their implementations. The present invention is exemplified in a number of implementations and applications, some of which are summarized below.

According to an example embodiment of the present invention, a specimen imaging system includes a light source, a light detector, a GRIN-lens type micro-optical probe and compensation optics. The probe can include a (GRIN) lens arrangement to direct light from the light source to a specimen, and to direct light from the specimen to the light detector. The compensation optics compensate for aberrations in the lens arrangement, and the light detector receives and detects light from the specimen, via the probe. The detector uses the detected light to present a signal characterizing the detected light as corrected for aberrations via the compensation optics (e.g., as corrected in application of the light to the tissue, and/or in response light received from the tissue).

In some embodiments, the compensation optics are micro-optics, integrated as part of the probe, and employ a single plano-convex or biconvex lens to correct for most or all lens aberrations. This approach is used to facilitate imaging and/or detection with tissue undergoing analysis, using a GRIN lens and using optics on a micro-optical scale (and thus implementable with a micro-optical probe, using optics having dimensions on the order of one to a few millimeters, or less). In this context, imaging is carried out with a micro-optical probe with corrections made in micro-optics, alleviating needs to use bulky optical systems.

According to another example embodiment of the present invention, a micro-optical imaging system facilitates two-photon microscopy of tissue in a specimen. The system includes a light source, a light detector, a wavelength-dependent dichroic, a micro-optical probe with a GRIN lens arrangement, and compensation optics. The light source directs stimulation photons to the dichroic, which passes the stimulation photons to the micro-optical probe. The micro-optical probe directs the stimulation photons to the tissue via the GRIN lens and further directs a photoemission response from the tissue towards the light detector via the dichroic. The compensation optics are located in the path of light between the light detector and the tissue and re-direct the stimulation photons to compensate for aberrations in the GRIN lens arrangement and focus a light spot to a target portion of the tissue. The dichroic passes photoemissions from the specimen towards the light detector as a function of the respective wavelengths of the photons and photoemissions. The light detector receives and detects the photoemissions from the specimen, via the probe, and presents a signal characterizing the detected photoemissions.

According to another example embodiment of the present invention, tissue in a specimen is imaged using a GRIN lens probe arrangement and compensation optics. A micro-optical probe including a GRIN lens arrangement is inserted into the tissue of a specimen to direct light from a light source to the tissue and to direct light from the tissue. Compensation optics redirect the light directed from the tissue by the probe to correct for aberrations in the GRIN lens arrangement, and pass the corrected light for analysis. The corrected light from the specimen is detected and a corrected signal characterizing the detected light as corrected for aberrations via the compensation optics is presented for analysis.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for a variety of imaging applications, and the invention has been found to be particularly suited for implementation with micro-optics type (e.g., gradient-refractive index (GRIN)) lenses. While the present invention is not necessarily limited to such applications and/or lenses, aspects of the invention may be appreciated through a discussion of various examples using this context.

According to an example embodiment of the present invention, corrective optics such as lenses and other optical components are implemented with a GRIN lens microscopic probe arrangement to image a specimen. The GRIN lens probe is generally small to facilitate microscopic analysis of a specimen; in some applications the GRIN lens probe has a diameter of less than about 2 mm, in other applications, the GRIN lens probe has a diameter of less than about 1 mm, and in other applications, has a diameter of about and/or less than about 350 microns. The corrective optics are located at a distal end of the GRIN lens probe arrangement, relative to the specimen undergoing analysis, leaving a portion of the GRIN lens near the specimen free. With this approach, desirable optical, size and weight characteristics of such a GRIN lens probe arrangement are realized while further compensating for undesirable GRIN lens attributes. The corresponding resolving power of the GRIN lens probe arrangement facilitates microscopy and microendoscopy applications. In addition, this arrangement further facilitates the optical sensitivity of the GRIN lens arrangement as well as the intensity of light at the GRIN lens system's focus.

In a more particular embodiment, the corrective optics consist of a single biconvex lens that can be implemented in the probe (i.e., the lens having a diameter of about 1 mm allows such implementation), and used as a single source to correct for about all aberrations in the GRIN lens. The correction of GRIN lens aberrations is thus carried out in micro-optical components, and can achieve diffraction-limited resolution by two-photon imaging. This approach also enhances fluorescence excitation efficiency, which can also be degraded by aberrations.

In one particular embodiment, a specimen is imaged via epifluorescence imaging with a GRIN lens system employing corrective optics that compensate for aberrations resulting from GRIN lens or lenses in the system. Compensating optics including a lens system are positioned on a side of the GRIN lens system that is distal to a specimen plane, leaving the portion of the GRIN lens system in proximity to the specimen unobstructed. The GRIN lens system includes a coverslip to contact the specimen, a high-numerical aperture GRIN lens with a pitch of less than about ¼ (e.g., for a corresponding working distance of a few hundred microns), and a lower-numerical aperture GRIN lens to provide magnification of the image. An image of fluorescence emissions from the specimen plane is projected to the back face of the GRIN lens system, where the compensating optics correct for some or all of the aberrations in the projected image. The compensating optics project the image to a tube lens and then onto a camera or through an eyepiece.

In another example embodiment, the above approach is implemented with two-photon imaging, such as with fluorescence microendoscopy. An approximately collimated, pulsed near-infrared laser beam is passed to the specimen via the compensating optics, which focus the laser to a spot near the distal end of the GRIN lens system. The laser beam is scanned using, for example, galvanometer-mounted mirrors, micromirrors, or another approach to translate the beam at the distal end of the GRIN lens system, causing the spot focused by the GRIN lens system to be scanned across the specimen plane. The compensating optical component serves to reduce the aberrations present in the spot that is focused by the GRIN lens in the specimen plane. For instance, one application involves using compensating optical components that correct for chromatic aberration in a GRIN lens, with optical components that exhibit chromatic dispersion tendencies that are opposite of that of the GRIN lens.

In some embodiments, the distance between the compensating optics and the GRIN lens system is varied to change the working distance of the GRIN lens system. For certain applications, the compensating optics compensate for aberrations in a different manner, or not at all, when this distance is varied. In this regard, aberration correction is selectively implemented via the positioning of the compensating optics.

The GRIN lens system includes one or more GRIN lenses, each with one or more arrangements, depending upon the application. In one example embodiment, the GRIN lens system includes a single GRIN lens, and in other embodiments the GRIN lens employs two, three or more GRIN lenses. In other example embodiments, the GRIN lens or lenses have various lengths, various pitch lengths, different numerical apertures, various focal lengths and working distances, and various diameters ranging from several microns to several centimeters. In each instance, the corrective optics are implemented to correct for aberrations relative to the arrangement, number and other characteristics of GRIN lenses.

Figure 1:
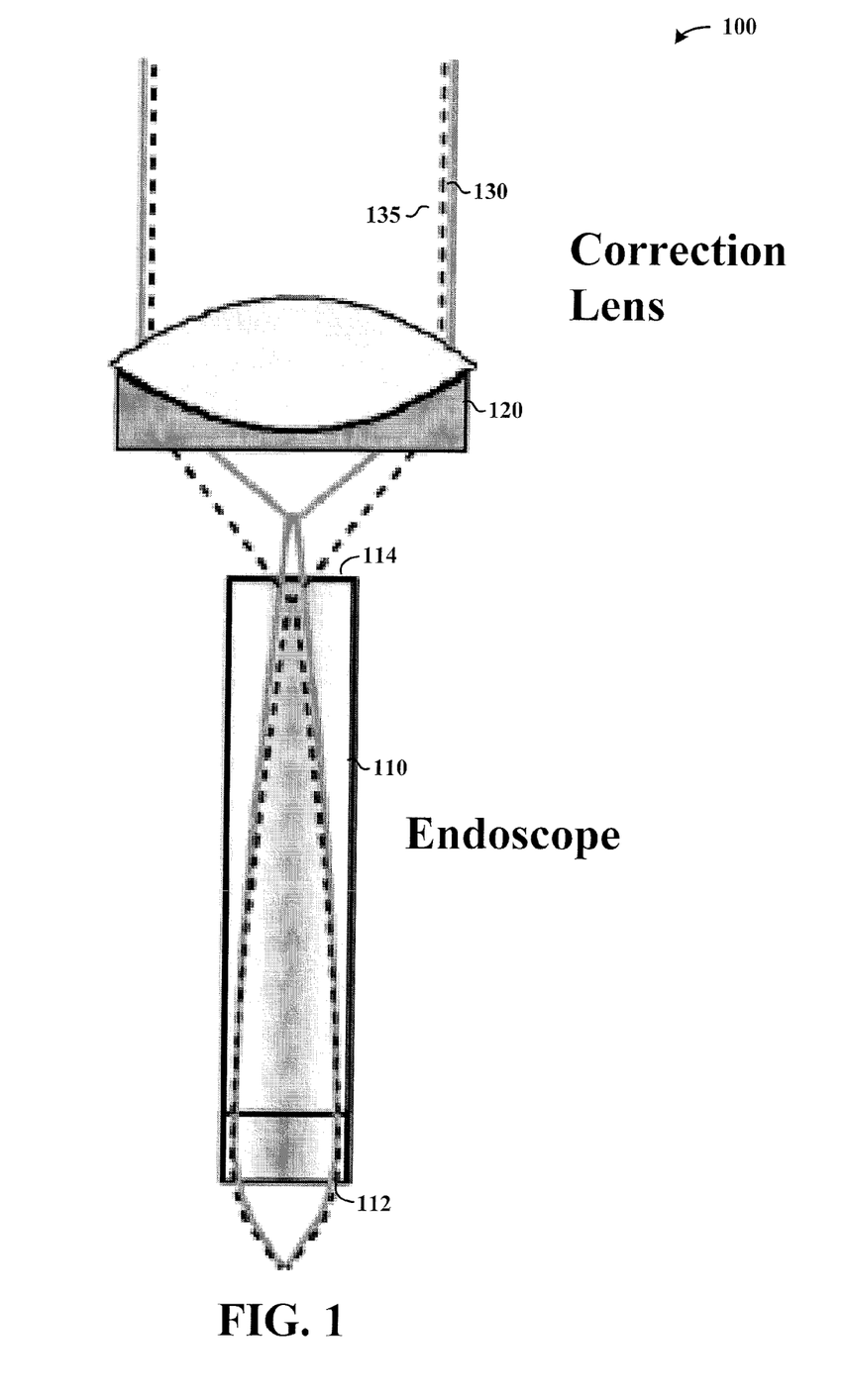
FIG. 1 shows a microendoscope probe arrangement with corrective optics, according to an example embodiment of the present invention.

Turning now to the figures, FIG. 1 shows a GRIN lens endoscope arrangement 100, according to another example embodiment of the present invention. The arrangement 100 includes an endoscope 110 having one or more GRIN lenses for passing light from a specimen near a first end 112 of the endoscope to a distal end 114 of the endoscope. A compensation arrangement 120 including a correction lens corrects for aberrations in the GRIN lenses of the endoscope 110.

Light is passed to a specimen via the correction lens 120 and endoscope 110. Light of a shorter wavelength is represented by solid lines including line 130, and light of a longer wavelength is represented by dashed lines including line 135. This light is passed via the correction arrangement 120, which counters wavelength-based aberrations in the GRIN lenses, such that both wavelengths target a similar (or the same) portion of the specimen undergoing analysis.

In some embodiments, the compensation arrangement 120 includes a doublet lens, and in other applications includes a triplet lens. With certain applications involving such lenses, residual spherical aberrations and coma are corrected, in addition to correcting for GRIN lens aberrations. For example, in one doublet lens embodiment, a crown glass convex lens of relatively low refractive index and dispersion is combined with a flint glass concave lens of higher index and dispersion. If $f_1$, $f_2$ and $V_1$, $V_2$ are the respective lens focal lengths and Abbe numbers (a measure of chromatic dispersion), then the Abbe condition for having the same focal length at the top and bottom of the spectral range is $f_1V_1 + f_2V_2 = 0$.

The Abbe condition is modified so $f_1V_1 + f_2V_2$ is not zero, and balances the chromatic aberrations from the GRIN lenses in the endoscope 110. In some applications, this Abbe condition is modified by changing the shape of the doublet used, and in other applications, by selecting glass materials for the doublet that facilitate this condition (e.g., rather than altering the doublet's shape) to mitigate spherical aberrations. For certain one- and two-photon imaging applications, separate chromatic correction lenses are also implemented with the compensation arrangement 120.

The lens or lenses in the compensation arrangement 120 include one or more types of lenses to suit particular applications. In some embodiments, a doublet that has a plano-convex shape is used to achieve an Abbe condition as discussed above. In some implementations, the plano-convex lens in the compensation arrangement 120 is a high-NA lens that uses a high refractive index glass such as an LaSFN9 lens (e.g., available from Edmund Optics of New Jersey, USA) to facilitate an NA of at least about 0.8.

In some embodiments involving the use of a high-NA plano-convex lens in the compensation arrangement 120, one or more approaches are used to correct for spherical aberrations introduced by the high-NA plano-convex lens. In some applications, curved lenses are used, at one or both of the compensation arrangement 120 and the endoscope 110, or elsewhere in the arrangement 100. In other applications, one or more GRIN rod lenses are used in the endoscope 110, having characteristics that facilitate the passage of light to correct spherical aberrations. One such GRIN rod lens has an approximate refractive index radial profile of $$n(r) = n_0 \left(1 - \frac{g^2}{2}r^2 + h_4(gr)^4 + \ldots\right),$$

with a central refractive index $n_0$, pitch parameter g, and $4^{th}$ order refractive index coefficient $h_4$. For implementation in connection with certain embodiments, the term $h_4$, and related GRIN rod lens characteristics, is adjusted or set to compensate for spherical aberration. In connection with these embodiments, it has been discovered that using such a GRIN rod lens with a refractive index radial profile, in connection with a plano-convex corrective lens, is useful for obtaining corrected images that exhibit desirable resolution. It has also been discovered that a single micro-optics biconvex lens connected to a GRIN lens, can correct for about all or all primary Seidel aberrations in the GRIN lens, and can do so without any further correction. In these contexts, the correction of aberrations in GRIN lenses used in micro-optical probes can be carried out at the micro-optical level (e.g., using a single biconvex lens having a diameter of about 1 mm), and without using additional compensation optics, which can be bulky and otherwise undesirable. In connection with these approaches, it has further been discovered that this approach enhances fluorescence excitation efficiency, which can be degraded by aberrations.

A variety of high-NA plano-convex lenses, and corresponding GRIN rod lens(es) are used to suit different applications. In one embodiment, a 1.2 mm diameter probe includes plano-convex microlenses that are about 4 mm in length and 1.0 mm in diameter, and that are made from a material such as BK7 (n=1.506) glass (e.g., as available from Edmund Optics as referenced above) or LaSFN9 (n=1.856) glass. A stainless steel sheath of about 0.1 mm thickness is used to provide structural support for the probe, and the probe can be used with selected spot sizes at working distances of about 300 μm in water.

Figure 2:
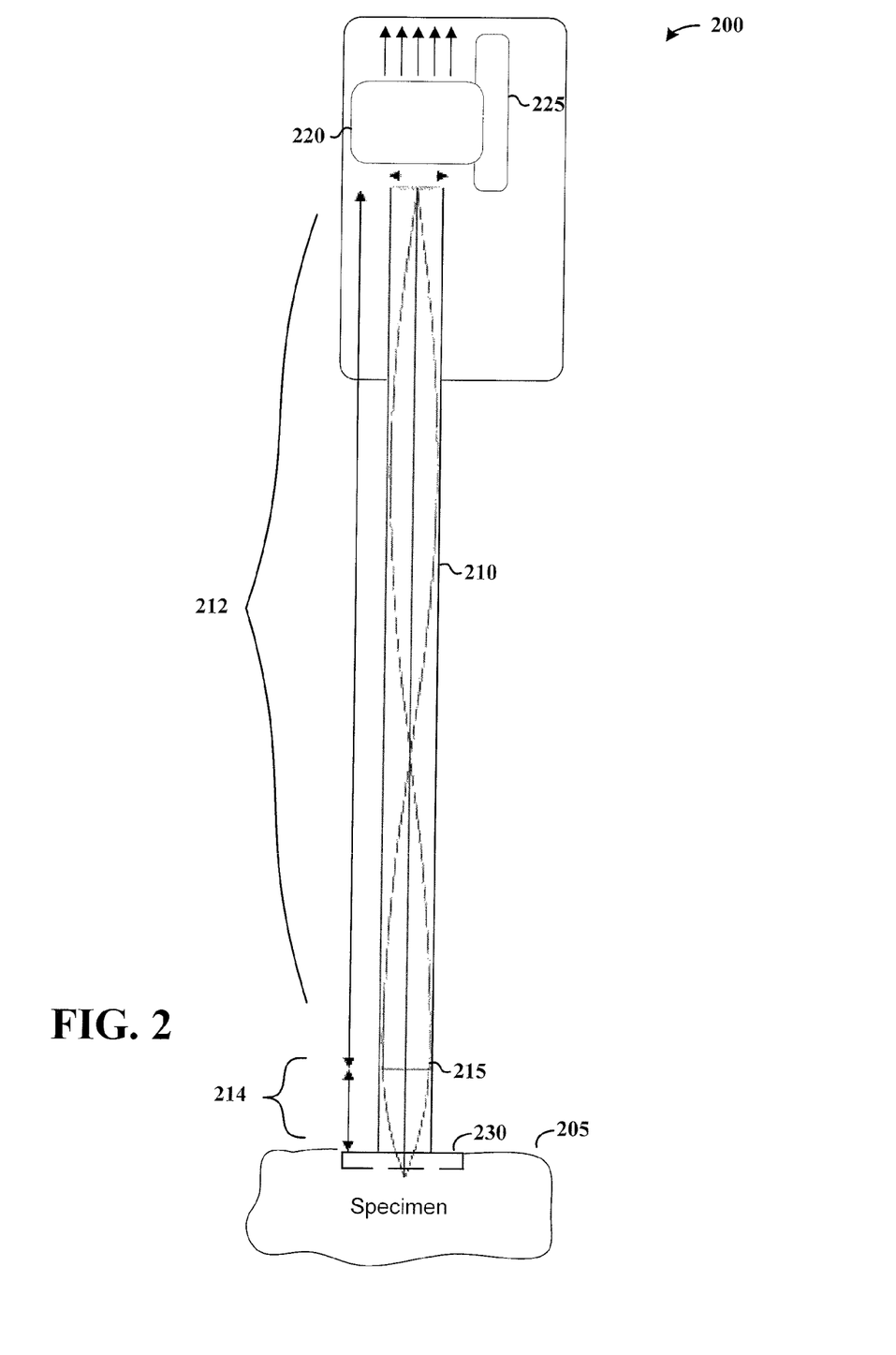
FIG. 2 shows another micro-optical probe arrangement with a GRIN lens, according to another example embodiment of the present invention.

In some applications, the endoscope 110 uses a relatively long relay lens (e.g., as shown in FIG. 2), with chromatic aberration in the endoscope dominated by the long relay lens. In these applications and for certain embodiments, the compensation arrangement 120 is set to compensate for the relay lens, as any other (relatively short) objective lenses used exhibit relatively low aberration. In this regard, a combination of such a long relay lens and compensation optics can be used for a variety of applications involving different objective lenses for different focus, while correcting for a substantial amount of aberrations in the GRIN lens arrangement.

In various embodiments, the GRIN lens arrangement 100 includes optical components in addition to one or more GRIN lenses as discussed above. These optical components may include, for example, as a coverslip, one or more mirrors, other lenses such as a ball lens or an asphere, diffractive optics, one or more optical fibers (e.g., single-mode fibers, multimode fibers, photonic crystal fibers, fiber lasers) or optical fiber bundles, a beamsplitter prism cube and a prism. In addition, one or more of the optical components of the GRIN lens arrangement 100 are coated with one or more optical coatings such as anti-reflective coatings. In some applications, additional components are fused to a GRIN lens, or are located in close vicinity to a GRIN lens (e.g., within a few millimeters or centimeters). In some applications involving additional optics, the compensation arrangement 120 compensates for undesirable characteristics such as aberrations that are exhibited by these additional optics.

In another example embodiment as related to the GRIN lens arrangement 100 and/or otherwise, a GRIN lens is polished or cut to a specific shape at either one of its ends. Such shapes include, for example, a cone, a cylinder with a smaller diameter than the GRIN lens, a sphere, or a flat angle (including a flat angle of zero degrees). In some applications, compensating optics compensate for aberrations introduced by the polishing.

A variety of approaches are implemented for making a GRIN lens arrangement such as the arrangement 100. In some embodiments, ray tracing simulations are used to simulate the operation of optical assemblies involving one or more correction lenses. In some embodiments, curved GRIN lens surfaces are micromachined.

Figure 3:
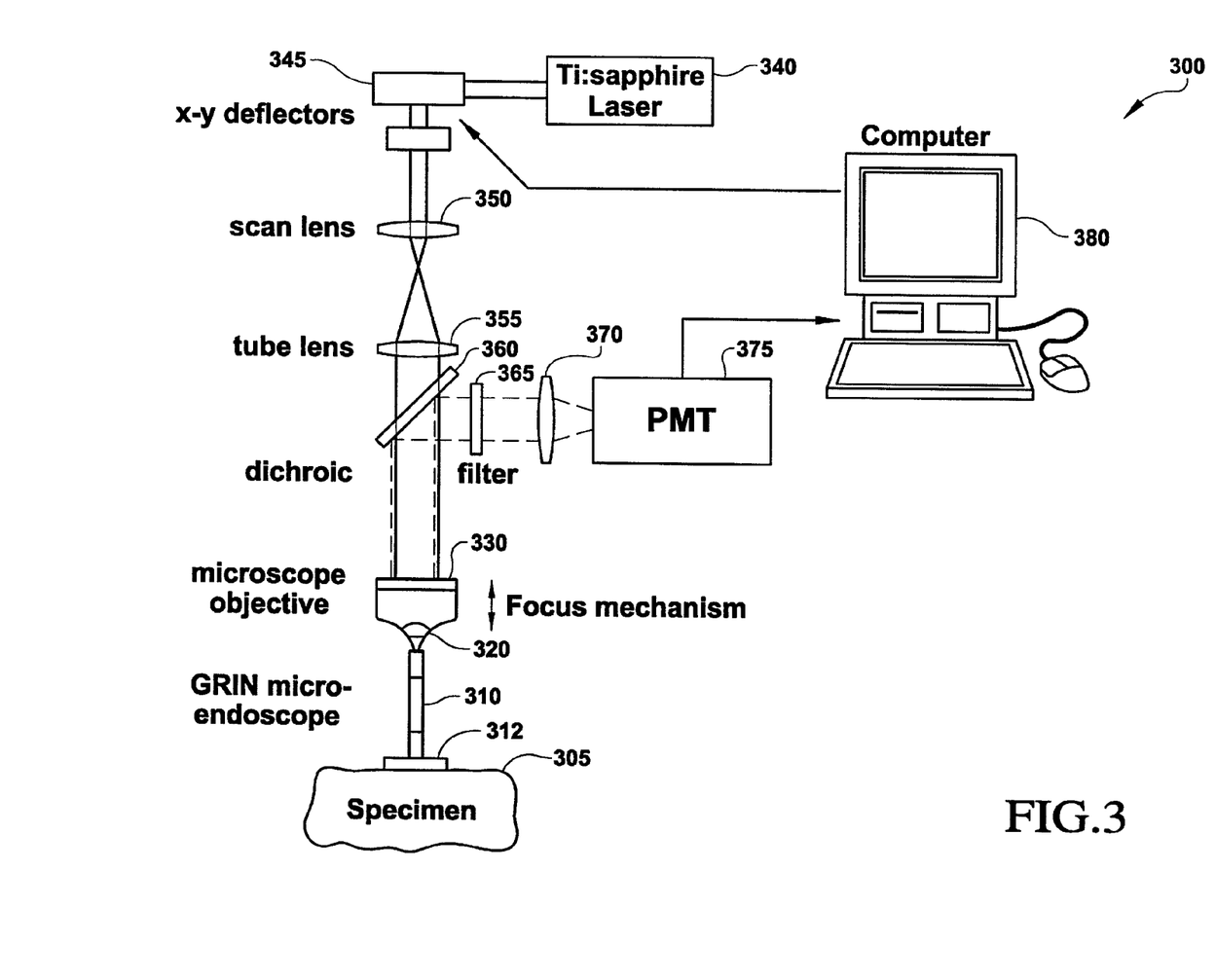
FIG. 3 shows a microendoscope probe system, according to another example embodiment of the present invention

FIG. 2 shows another micro-optical probe arrangement 200 with adjustable compensation optics, according to another example embodiment of the present invention. The micro-optical probe arrangement 200 includes a GRIN lens arrangement 210, compensation optics 220 and an actuator 225 to set the position of the compensating optics relative to the GRIN lens arrangement 210. Light passed into the GRIN lens arrangement 210 is focused by an optical component 215 to a plane in the specimen 205, through a coverslip 230. That is, an upper portion 212 of the GRIN lens arrangement 210 is implemented as a relay lens, and a lower portion 214 of the GRIN lens arrangement 210 focuses light to the specimen 205. As described above and for certain applications, the lower portion 214 is replaced with one or more of a variety of arrangements to facilitate certain applications, with the compensation optics 220 set to compensate for aberrations in the relay lens 212.

Light from the specimen 205 is in turn passed via the coverslip 230, GRIN lens arrangement 210 and compensation optics 220 for use in imaging the specimen. In some applications, the coverslip 230 has a thickness of about 0.15 mm, and a refractive index of about 1.526, for imaging a tissue specimen with a refractive index of about 1.38.

Generally, the actuator 225 positions the compensation optics 220 to set the working distance of the micro-optical probe arrangement 200. The position of the compensation optics 220 is chosen to facilitate compensation for certain applications, such as for directing source light to the specimen, directing response light from the specimen for imaging, or for other approaches. For example, where the focus depth into the specimen 205 changes, the position of the compensation optics 220 is set accordingly. In this regard, and for various applications, the compensation optics are implemented as a microscope objective (e.g., as shown in FIG. 3), with selective, specific tailoring to facilitate probe-based analysis and related device characteristics.

In some applications, the alignment of the GRIN lens arrangement 210 is controlled using manual visualization and corresponding alignment involving one or more of mechanical and manual inputs. In other applications, non-manual alignment approaches are used to achieve a relatively higher degree of alignment reliability.

As discussed above, a variety of GRIN lenses and lens arrangements are used for different example embodiments. In one embodiment, the GRIN lens arrangement 210 includes a lithium relay lens (GTLIVIS), with a 0.75 pitch and cut to about 18.443 mm with the following characteristics:

$n_0$=1.523920,
$n_{r2}$=−0.49329±0.02,
$n_{r4}$=0.000700,
$K_{11}$=0.0205,
$K_{12}$=−0.02256,
$\Lambda_{ref}$=0.67 µm,
$\Lambda_{min}$=0.40 µm, and
$\Lambda_{max}$=1.0 µm in accordance with the following equations $$n_{ref} = n(\lambda_{ref}) = n_0 + n_{r2}r^2 + n_{r4}r^4 \qquad \text{Equation 1}$$

$$r^2 = x^2 + y^2, \text{ and} \qquad \text{Equation 2}$$

$$n(\lambda)^2 = n(\lambda_{ref})^2 + \frac{K(\lambda^2 - \lambda^2_{ref})}{\lambda^2}, \text{ where } K = K_{11} + K_{12}(n_{ref})^2. \qquad \text{Equation 3}$$

The coverslip 230 for this embodiment is about 0.15 mm thick, with a working distance of about 100 microns in the specimen 205 for a silver objective as described, for example, in connection with an example embodiment below referencing FIG. 3.

FIG. 3 shows a system 300 for micro-optical probing of a specimen 305, according to another example embodiment of the present invention. The system 300 includes a GRIN micro-endoscope arrangement 310 that directs light to and from the specimen 305 via a coverslip 312. Light is passed to and from the micro-endoscope arrangement 310 via a microscope objective 330 (adapted to move for focusing as shown by arrows).

A laser 340 supplies light to the micro-endoscope arrangement 310 for illuminating and/or stimulating the specimen 305. Light from the laser 340 is passed through x-y deflectors 345, a scan lens 350 and a tube lens 355 to a dichroic 360 (e.g., a beam splitter).

Light from the specimen 305 is passed from the microscope objective 330 to the dichroic 360, which directs the light to a light detector 375, shown here by way of example as a photomultiplier tube. A filter and lens 365 and 370 are respectively located in the light path between the dichroic 360 and the photomultiplier tube 375. The photomultiplier tube 375 outputs data characterizing the light to a computer 380, which creates an image to facilitate the analysis of the specimen 305. In some applications, the computer 380 also controls the x-y deflectors 345 for controlling the application of light to the specimen 305.

The system 300 can be used with various microscopy equipment and applications. In some embodiments, the system 300 is implemented with a conventional two-photon microscope, such as available from Prairie Technologies of Middleton, Wis. With such applications, the objective 330 can be implemented with a 20×0.5 NA objective (e.g., an Epiplan Neofluar objective available from Zeiss of Thornwood, N.Y.) or a 50×0.5 NA objective (e.g., the Leica Plan objective available from Leica Microsystems of Bannockburn, Ill.) to couple light with the micro-endoscope arrangement 310.

The system 300 is implemented with one or more of a variety of imaging applications. In one application, neuronal dendritic spines in the hippocampus of live rats and mice are imaged. The rats and mice exhibit punctate fluorescence in hippocampal dendritic spines as introduced by adenoviral vectors and transgenic methods, respectively. In some applications, neurons are imaged in transgenic mice expressing GFP-actin in hippocampal dendritic spines, and in rats expressing GFP-actin under the control of adenoviral vectors. Other imaging applications involve analysis with similar test animals, humans and others. For general information regarding optical analysis, and for specific information regarding various approaches that may be implemented in connection with these and other example embodiments described herein, such as for coupling the GRIN micro-endoscope arrangement 310 to a live being, reference may be made to U.S. patent application Ser. No. 11/338,598 to Schnitzer, et al., entitled "Live Being Optical Analysis System and Approach" and filed on Jan. 24, 2006 (now U.S. Pat. No. 8,788,021), which is fully incorporated herein by reference.

In some applications, the dichroic 360 passes light in accordance with wavelength or other characteristics. For instance, where the laser 340 applies pulses of light at a certain wavelength for two-photon microscopy, the dichroic 360 simply passes the pulses through to the microscope objective 330. When response light from the specimen 305 (i.e., a photoemission) of a different wavelength is passed to the dichroic 360 from the microscope objective 330, the dichroic directs the response light towards the photomultiplier tube 375. One such example application involves the correction of aberrations in the 750-1000 nm wavelength range for diffraction-limited focusing in the specimen 305.

Corrective optics, such as an arrangement of lenses and/or other optical devices, are placed in the path of one or both of source light from the laser 340, and response light from the specimen 305, to correct for aberrations in the GRIN micro-endoscope arrangement 310. In some applications, the compensation optics are located at position 320 to facilitate the focus of laser light to a plane in the specimen 305 by compensating for aberrations in the GRIN micro-endoscope 310 (i.e., altering the light path before the light is passed through the micro-endoscope). The compensation optics further compensate for aberrations in the GRIN micro-endoscope 310 in altering response light from the specimen as passed to the photomultiplier tube 375. In other applications, corrective optics are placed at other locations, such as between the microscope objective 330 and the dichroic 360, between the dichroic and the photomultiplier tube 375, or between the dichroic and the laser 340. In one particular application, the microscope objective 330 includes the compensation optics and/or is compensating. Generally, the system 300 is implemented with the corrective optics in one or more of a multitude of locations, depending upon the application, and in accordance, for example, with one or more example embodiments as described above.

In one particular embodiment, the microscope objective 330 in the arrangement shown in FIG. 3 includes a silver objective (GTAG) with the following attributes:

$n_0 = 1.628930$,
$n_{r2} = -0.326737 \pm 0.02$,
$n_{r4} = 0.057900 \pm 0.02$,
$K_{11} = 0.11098$,
$K_{12} = -0.06172$,
$\Lambda_{ref} = 0.67$ μm,
$\Lambda_{min} = 0.40$ μm, and
$\Lambda_{max} = 2.0$ μm Such an objective is implemented, for example, in accordance with the above-referenced Equations 1-3 discussed with the lithium relay lens, as applicable to FIG. 2. The GTAG objective is thus implemented to facilitate application with endoscopic analysis.

In another exemplary embodiment, the GRIN micro-endoscope arrangement 310 has a pitch length that is reduced (via removal of ¼ pitch length), and the nr4 parameter in the GRIN microlens component is tuned to this length to facilitate plug and play use in miniaturized microscopes.

The endoscope applications described herein are implemented with a variety of approaches, including both one-photon and two-photon endoscopy, with correction optics arranged relative to the endoscope to suit specific applications to which the endoscope is applied, and correspondingly, to correct for undesirable optical characteristics associated with these applications. Some applications to which these endoscopes and related corrective optics are applied include multi-color imaging approaches to image multiple biochemical species for simultaneous analysis, and other applications involve optics facilitating near diffraction-limited optical resolution for obtaining images of fine biological structures. Other applications involve tracking submicron structures such as mitochondria or dendritic spines for high-resolution biomedical diagnostics. Still other applications involve imaging low-signal fluorophores and chromophores, such as voltage sensitive dyes, genetically encoded calcium indicators, as well as intrinsic signals.

Other applications involve fluid and/or electrical analysis coupled with the optical approaches described herein. For example, some embodiments involve fluid exchange with the endoscope, such as micro-fluidic delivery and sampling for on-line delivery of drugs and recovery of fluid specimens for (subsequent) off-line biochemical or cellular analyses. Electrical approaches to which various embodiments are directed include endoscope arrangements with auxiliary probes to electrically couple with a subject undergoing optical analysis, such as for on-line electrophysiological measurements using voltage recordings made concurrently with imaging and correlation of the imaging and voltage recordings. Still other approaches involve the use of adenoviral vectors in-vivo with an injection protocol optimization. For general information regarding endoscope applications, and for specific information regarding applications involving fluid and/or electrical application with imaging, reference may be made to U.S. patent application Ser. No. 11/334,769 (Schnitzer et. al), entitled "Optical Analysis System and Approach Therefor" and filed on Jan. 18, 2006 (now U.S. Pat. No. 8,346,346), which is fully incorporated herein by reference.

In other embodiments and applications, variations of the above-described (GRIN) micro-endoscope probe systems can be implemented. Such alternative (very small) lens systems may be implemented to have acceptable features and overall diameters as described above. In view of the above description, such alternative embodiments and applications would be appreciated with reference to microscopic endoscopes using lens technology described in U.S. Pat. No. 5,161,063 (with reference to Olympus scopes having diameters at about 700 microns). For further information regarding variations, other embodiments and applications, reference may be made to, "In Vivo Imaging of Mammalian Cochlear Blood Flow Using Fluorescence Microendoscope", Otology and Neurotology, 27:144-152, 2006, "In Vivo Brain Imaging Using a Portable 3.9 Gram Two-photon Fluorescence Microendoscope", Optics Letters, Vol. 30, No. 17, Sep. 1, 2005, and the following U.S. Patent Publications No. 20040260148 entitled "Multi-photon endoscopic imaging system"; No. 20040143190 entitled "Mapping neural and muscular electrical activity"; No. 20030118305 entitled "Grin fiber lenses"; No. 20030117715 entitled "Graded-index lens microscopes"; No. 20030031410 entitled "Multi-photon endoscopy"; No. 20020146202 entitled "GRIN fiber lenses"; and No. 20020141714 entitled "Grin-fiber lens based optical endoscopes".

Experimental Embodiments

The following discussion characterizes several example experimental embodiments, some of which may be implemented in connection with one or more of the embodiments described herein. Such approaches may be used, for example, in the design, fabrication, implementation and operation of microlens-based arrangements.

Resolution

The two-photon resolution of the GRIN assemblies is examined in connection with various embodiments. Sub-resolution 0.2 μm fluorescent beads are imaged using 920 nm excitation wavelengths at average powers of about 4-8 mW in the specimen plane. The optical distance between the microscope objective and proximal face of the GRIN assembly is set to the optimal design distance by imaging the proximal face at low excitation power and moving a known distance away with a motorized stage. Sample position is independently controlled using a piezoelectric positioning system. Three-dimensional image stacks are taken at 0.21 μm increments. The in-focus lateral magnification is measured within the local field of view (Figure XX) for each image stack. Bead profiles are fit to Gaussian functions, and full-width half-max (FWHM) measurements are calculated.

Measured results are compared to the theoretical diffraction limited imaging case, and to optical simulations of the microendoscope (Zemax). The measured system point spread function (PSF) and thus resolution is determined by the convolution of the two-photon microscope PSF and the microendoscope PSF. Approximating the intensity PSFs as Gaussian functions, the variances obey the following relation, $$\sigma^2_{system} = \sigma^2_{endoscope} + \left(\frac{\sigma_{microscope}}{M_{endoscope}}\right)^2$$

with microendoscope magnification $M_{endoscope}$. The predicted two-photon resolution is determined by the variance of the intensity-squared system PSF, for which Gaussian functions have ½ decrease in variance. Individual variances are calculated and converted to FWHMs in the paraxial approximation by using the NAs of the microscope coupling objective and the microendoscope. Full utilization of the lens NAs is assumed, which in practice involves overfilling of the coupling objective. The endoscope magnifications on optical axis are measured and are consistent with predictions from ray tracing analysis. In optical simulations, Huygens wavelet analysis is used to determine the PSF of a point source above the GRIN lens to an image in the sample plane below the plano-convex lens. Experimental results are shown in the following table:

by quadratic fit. The microscope system can affect excitation efficiency by modulating focal volume, intensity distribution, and collection efficiency:

The fluorescence signal, F(t), $$\langle F(t) \rangle = C\phi \int_v dr I^2(r, t)$$

is determined by fluorophore specific parameter comprising C, microscope collection efficiency Φ, and the volume integrated laser intensity-squared I function, a measure of excitation efficiency. With higher numerical apertures, collection efficiency is improved by using a larger solid angle of light collection. Furthermore, in the diffraction limit, as well as the limit of Gaussian waves, the excitation efficiency is not affected by numerical aperture.

After normalizing the volume integrated PSFs within the focal volume, the volume integral of the square of the PSFs are calculated, to provide a parameter relevant to two-photon excitation.

Comparison in Tissue

Imaging characteristics of microendoscopes are tested by visualizing fixed samples of hippocampal pyramidal neurons that express green fluorescent protein under the Thy-1 promoter. This preparation allows the direct comparison of images taken from different microendoscopes within the same field of view. While original singlet lenses are able to image dendritic branches, resolution studies are affected by: 1) the axial resolution and related excited fluorescence outside an intended focal volume, which can increase background intensity levels, and 2) lateral resolution for visualizing spines.

Excitation Efficiency and Magnification

As similar to the above discussion, the fluorescence generated during two-photon excitation can be described by:

$$\langle F(t) \rangle = C\phi \int_v dr I^2(r, t)$$

| Endoscope | Ideal (Zemax) magnification | | Ideal endoscope | | Ideal System | | Measured System | |
|---|---|---|---|---|---|---|---|---|
| | Lateral | Axial | lateral | Axial | lateral | axial | lateral | Axial |
| Singlet (NA = 0.45) | 0.98 | 0.72 | 0.77 | 7.69 | 1.00 | 9.91 | 1.48 | 12.2 |
| BK7 (NA = 0.65) | 1.41 | 1.50 | 0.53 | 3.68 | 0.69 | 4.76 | 0.75 | 7.71 |
| LaSFN9 (NA = 0.85) | 1.86 | 2.58 | 0.41 | 2.15 | 0.53 | 2.77 | 0.60 | 2.82 |

High NA lenses are designed to provide near diffraction-limited performance. Experimental performance deviates more strongly as magnification decreases, suggesting a non-diffraction limited microscope PSF.

Excitation Efficiency

The fluorescence capabilities of the microendoscope system are examined. A solution of 1 μM Alexa 594 in water is excited at various laser powers at 920 nm, and the collected signal intensities are first verified to be of two-photon origin where C represents fluorophore-specific constants, φ represents microscope collection efficiency, and I represents laser excitation intensity over a focal volume V. GRIN probe operation, in connection with various embodiments, is represented by desirable collection efficiency and a $I^2$ within a focal volume.

Theoretical excitation efficiencies of high-resolution microendoscopes, according to one or more embodiments, are compared to a ~0.5 NA singlet microendoscope. A solution of 1 μM Alexa 594 is excited at various laser powers and the resulting signal intensities are fit to quadratic functions.

The microscope system can affect excitation efficiency by modulating focal volume, intensity distribution, and collection efficiency.

The magnification of a GRIN lens system, in accordance with one or more embodiments, is measured in the lateral and axial dimensions using 0.1 µm fluorescent bead samples. In the lateral dimension, the microscope system is moved a known distance, such as 1.5 µm, and centroid displacement per distance traveled is computed. A series of displacements are measured and averaged. The endoscope lateral magnification is defined as the ratio of the measured microendoscope displacement to measured microscope displacement.

Axial magnification is measured by controlling objective position and sample position relative to a fixed microendoscope. Objective absolute position is determined by focusing the objective's image plane to the proximal glass interface of the endoscope. The sample position is adjusted until the sample is in focus through the coupling objective and microendoscope. The absolute position can be taken as that of the design working distance for the microendoscope. Sample position is measured as a function of objective position. The slope of this relation was used to calculate magnification.

Magnification figures are compared based on three sources: experimental measurements, theory, and ray matrix analysis. The resolution capability of a GRIN microendoscope system is a function of the magnification of the endoscope and the underlying microscope system, and facilitates the imaging of a point source.

Representation of Refractive Index

Several conventions for representing the index of refraction in GRIN lenses exist:

$$n(r) = n_{r0} + n_{r2} r^2 + n_{r4} r^4 + \ldots,$$

$$n(r) = n_0 \sqrt{1 - g^2 r^2 + h_4 g^4 r^4 + \ldots}.$$

With Taylor expansion about r=0, $$n(r) = n_0 \left( 1 - \frac{g^2}{2} r^2 + \frac{h_4 g^4}{2} r^4 + \ldots \right).$$

This will give example relationships between $(n_{r2}, n_{r4})$ and $(g, h_4)$.

Fluorescence Generation $$\langle F(t) \rangle = \left( \frac{1}{2} \eta C \sigma_2 \right) \phi \langle I_0^2(t) \rangle \int_V dr S^2(r, t)$$

$$\langle F(t) \rangle = \left( \frac{1}{2} \eta C \sigma_2 \right) \phi \int_V dr I^2(r, t)$$

(collectively $\eta$, $C$, $\sigma_2$ fluorescence quantum efficiency, concentration, and two-photon absorbance cross-section)

Magnification a. Simulation

The following table presents example simulated axial and lateral magnifications of the endoscopes using Zemax:

| Endoscope | Lateral magnification | Axial magnification |
|---|---|---|
| Singlet | 0.98 | 0.72 |
| BK7 | 1.41 | 1.50 |
| LaSFN9 | 1.86 | 2.58 | b. Ray Matrix Calculation

Figure 4:
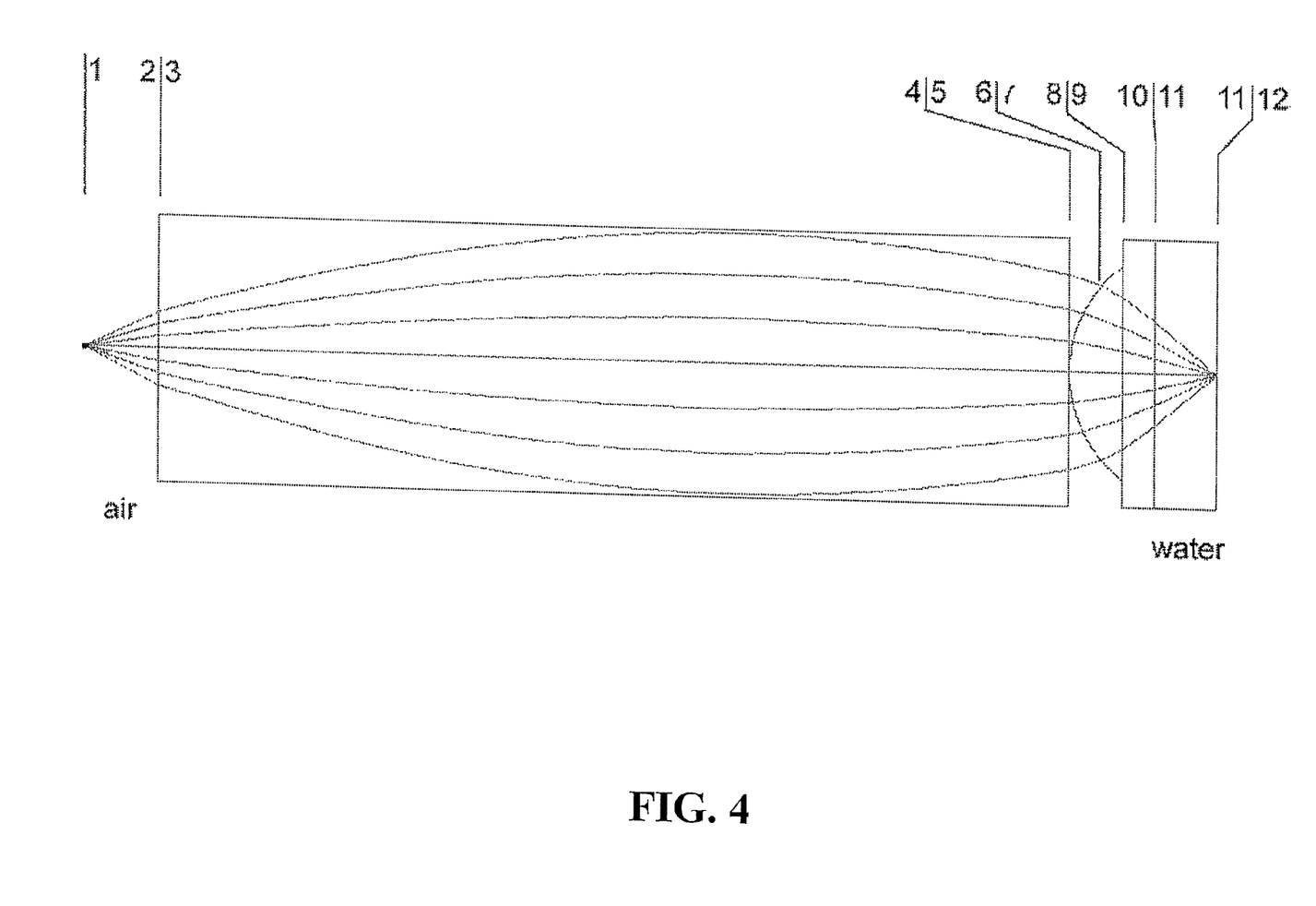
FIG. 4 shows a ray-tracing approach, according other example embodiments of the present invention.

The high resolution microendoscopes can be understood also by using ray transfer matrix analysis. Rays at (x, x') in the image plane originate from (y, y') at the object plane according to FIG. 4 and the following:

$$\begin{bmatrix} y \\ y' \end{bmatrix} = \begin{bmatrix} 1 & d_{object} \\ 0 & 1 \end{bmatrix} \begin{bmatrix} 1 & 0 \\ 0 & \frac{n_c}{n_w} \end{bmatrix} \begin{bmatrix} 1 & d_c \\ 0 & 1 \end{bmatrix} \begin{bmatrix} 1 & 0 \\ 0 & \frac{n_{ball}}{n_c} \end{bmatrix} \begin{bmatrix} 1 & d_{ball} \\ 0 & 1 \end{bmatrix} \begin{bmatrix} 1 & 0 \\ -\frac{n_{ball}-1}{r_{ball} n_{ball}} & \frac{1}{n_{ball}} \end{bmatrix}$$

$$\ldots \begin{bmatrix} 1 & 0 \\ 0 & 1 \end{bmatrix} \begin{bmatrix} 1 & 0 \\ 0 & n_0 \end{bmatrix} \begin{bmatrix} \cos(gL) & \sin(gL)/g \\ -g \sin(gL) & \cos(gL) \end{bmatrix} \begin{bmatrix} 1 & 0 \\ 0 & \frac{1}{n_0} \end{bmatrix} \begin{bmatrix} 1 & d_{image} \\ 0 & 1 \end{bmatrix} \begin{bmatrix} x \\ x' \end{bmatrix} =$$

$$\begin{bmatrix} A & B \\ C & D \end{bmatrix} \begin{bmatrix} x \\ x' \end{bmatrix}$$

When used for imaging, rays from x should arrive at y, independent of x', which requires B=0. The lateral magnification is given by 1/A subject to the imaging constraint. The relationship between lateral and axial magnifications of a lens in the paraxial approximation can be shown to be $$M_{axial} = M_{lateral}^2 \frac{n_{image}}{n_{object}},$$

where n represents the refractive indices of the image and object media. This relationship holds true in the paraxial limit as shown by Zemax simulations above. This matrix is calculated for several high-resolution microendoscope designs. The table below provides example roughly-determined parameters used and resulting magnifications:

| Lens | Image WD | Object WD | GRIN L | GRIN n0 | GRIN n2 | Lateral magnification | Axial magnification |
|---|---|---|---|---|---|---|---|
| Singlet | 50 | 300 | | | | | |
| BK7 | 50 | 300 | 3.62 | 1.6289 | −0.327 | 1.46 | 1.602 |
| LaSFN9* | 274 | 230 | 3.37 | 1.6289 | −0.327 | 2.28 | 3.90 |
| LaSFN9 Koenig | 50 | 50 | 3.80 | 1.6289 | −0.351 | 1.87 | 2.62 |

*Note:
in the paraxial limit, desirable pitch length is about 3.62 mm, resulting in lateral magnification of 2.32.

Resolution a. System Resolution and Microendoscope Resolution

For imaging systems, the imperfections incurred through the optical elements can be described by a point spread function (PSF). An intermediate image $I_{in}$ of object O generated using a microendoscope has the form:

$$I_{in}(x',y',z')=O(x,y,z)*PSF_{endoscope}(x,y,z)$$

subject to endoscope magnification (for ~½ pitch elements, image inversion occurs)

$$x'=-M_{lateral}x, y'=-M_{lateral}y, z'=-M_{axial}z.$$

This intermediate image is collected by a conventional two-photon microscope, characterized by a second PSF:

$$I_{image}(x,y,z)=(O*PSF_{endoscope})(x',y',z')*PSF_{microscope}(x,y,z).$$

For multiphoton excitation, one can approximate the PSF with a Gaussian form for both the microscope optics and the microendoscope:

$$PSF_{endoscope}(x,y,z) \approx \exp\left(-\frac{2(x^2+y^2)}{\omega_{0,endoscope}^2} - \frac{2(z^2)}{z_{0,endoscope}^2}\right)$$

$$PSF_{microscope}(x,y,z) \approx \exp\left(-\frac{2(x^2+y^2)}{\omega_{0,microscope}^2} - \frac{2(z^2)}{z_{0,microscope}^2}\right)$$

This simplifies the convolution, and the following variance relation can be obtained:

$$\sigma_{system}^2 = \sigma_{endoscope}^2 + \left(\frac{\sigma_{microscope}}{M_{endoscope}}\right)^2$$

This expression provides the relative contributions to the system PSF arising from the GRIN endoscope and the microscope. In microendoscope systems where low magnification of the object occurs, microscope aberrations contribute significantly to the system resolutions. In high magnification microendoscopes, the resolutions are primarily limited by endoscope aberrations.

The PSF used in the above equations is the intensity PSF. While the two-photon excitation is dependent on the square of excitation intensity, image formation in the intermediate plane is not an intensity-squared process. Thus to calculate the two-photon resolution, the system intensity-PSF is calculated and the result is squared.

In the approximation of Gaussian intensity distributions, the intensity-squared distribution is also Gaussian and one would expect a sqrt(2) improvement in the FWHM estimation. This improvement is verified in the analytical treatment of lateral resolutions using Airy distributions.

b. Measures of Resolution

Several measures of resolution exist. Generally, resolution represents the minimum distance by which two objects can be distinguished in an optical system. The point spread function (PSF) is used in determining the resolution of a system. In a diffraction limited system in-focus, the PSF takes the form of an Airy distribution.

Several criteria exist for examining the minimum resolvable distance between two closely spaced Airy distributions. Example criteria include the Rayleigh, Full-width half-maximum (FWHM) and Sparrow criteria.

1. Rayleigh criterion—the distance between the central maximum and the first minimum of the PSF. This is the standard theoretical estimate of resolution in diffraction limited systems, in which Airy distributions are used. In such systems formulas for Rayleigh distance (also called Abbe limit) exist:

$$\delta r = 0.61 \frac{\lambda}{NA}$$

$$\delta z = 2\frac{\lambda}{n}\left(\frac{n}{NA}\right)^2 = 2n\frac{\lambda}{NA^2}$$

It is noteworthy that the axial intensity distribution of diffraction limited systems is not strictly that of an Airy distribution, but of a Sinc-squared distribution. Also of note, the Rayleigh criterion does not provide an improvement when calculated for intensity-squared PSFs over intensity PSFs.

A table of Rayleigh resolutions is provided for $\lambda$=920 nm:

| Numerical Aperture | Refractive index | Lateral (μm) | Axial (μm) |
|---|---|---|---|
| 0.50 | 1.0 | 1.12 | 7.36 |
| 0.50 | 1.33 | 1.12 | 9.79 |
| 0.65 | 1.0 | 0.86 | 4.35 |
| 0.65 | 1.33 | 0.86 | 5.66 |
| 0.85 | 1.0 | 0.69 | 2.54 |
| 0.85 | 1.33 | 0.69 | 3.31 |

2. Full-width half-maximum FWHM—as defined. This measure is generally easier to experimentally determine. It is also smaller than the Rayleigh criterion, and thus places less demand on contrast when resolving two structures.

$$FWHM_{1-p,lateral} = 2\frac{1.618}{2\pi}\frac{\lambda}{NA} \approx 0.510\frac{\lambda}{NA}$$

$$FWHM_{2-p,lateral} = 2\frac{1.162}{2\pi}\frac{\lambda}{NA} \approx 0.379\frac{\lambda}{NA}$$

$$FWHM_{1-paxial} = 2\frac{5.566}{2\pi}\frac{\lambda n}{4n^2\sin^2(\alpha/2)} \approx 1.772n\frac{\lambda}{NA^2}$$

$$FWHM_{2-paxial} = 2\frac{4.0075}{2\pi}\frac{\lambda n}{4n^2\sin^2(\alpha/2)} \approx 1.273n\frac{\lambda}{NA^2}$$

Note that an epi-fluorescence axial resolution is not well-defined.

3. Sparrow criterion—in a situation where two Airy distributions are separated by some distance, the Sparrow limit is the minimum distance at which point the summed distribution exhibits a local central minimum.

c. Diffraction-Limited Estimates of Resolution for Microendoscope Systems

Based on the previous tables, a theoretical system resolution is calculated for two-photon microendoscopy in water. The coupling objective used is assumed to be a 0.50 numerical aperture operated in air. All resolutions in this table are based on the Rayleigh criterion (intensity PSF).

| Endoscope | $\sigma_{endoscope, lateral}$ | $\sigma_{system, lateral}$ | $\sigma_{endoscope, axial}$ | $\sigma_{system, axial}$ |
|---|---|---|---|---|
| Singlet (NA = 0.45) | 1.12 | 1.62 | 9.79 | 12.48 |
| BK7 (NA = 0.65) | 0.86 | 1.17 | 5.66 | 7.49 |

-continued

| Endoscope | $\sigma_{endoscope, lateral}$ | $\sigma_{system, lateral}$ | $\sigma_{endoscope, axial}$ | $\sigma_{system, axial}$ |
|---|---|---|---|---|
| LaSFN9 (NA = 0.85) | 0.61 | 0.85 | 3.31 | 4.36 |

In order to compare experimentally determined resolution estimates, the intensity FWHM criteria are also shown for the same systems:

| Endoscope | $\sigma_{endoscope, lateral}$ | $\sigma_{system, lateral}$ | $\sigma_{endoscope, axial}$ | $\sigma_{system, axial}$ |
|---|---|---|---|---|
| Singlet (NA = 0.45) | 1.04 | 1.42 | 10.71 | 14.02 |
| BK7 (NA = 0.65) | 0.72 | 0.98 | 5.13 | 6.72 |
| LaSFN9 (NA = 0.85) | 0.55 | 0.75 | 3.00 | 3.92 |

Lastly, the FWHM for the intensity-squared PSFs:

| Endoscope | $\sigma_{endoscope, lateral}$ | $\sigma_{system, lateral}$ | $\sigma_{endoscope, axial}$ | $\sigma_{system, system}$ |
|---|---|---|---|---|
| Singlet (NA = 0.45) | 0.77 | 1.00 | 7.69 | 9.91 |
| BK7 (NA = 0.65) | 0.53 | 0.69 | 3.68 | 4.76 |
| LaSFN9 (NA = 0.85) | 0.41 | 0.53 | 2.15 | 2.77 | d. Analytic Forms for PSF in Diffraction Limited Systems

In fluorescence approaches, the imaging point spread function is determined by the excitation intensity distribution:

$$I_{1-p}(u, v) = \left| 2 \int_0^1 J_0(v\rho) \exp(iu\rho^2/2) \rho d\rho \right|^2$$

with the optical coordinates:

$$v = \frac{2\pi r n \sin\alpha}{\lambda}$$

$$u = \frac{8\pi z n \sin^2(\alpha/2)}{\lambda}$$

In-focus PSF can be simplified to:

$$I_{lateral}(v) = \left(\frac{2J_1(v)}{v}\right)^2, \text{ and}$$

$$I_{axial}(u) = \left(\frac{\sin(u/4)}{u/4}\right)^2.$$

Figure 5A:
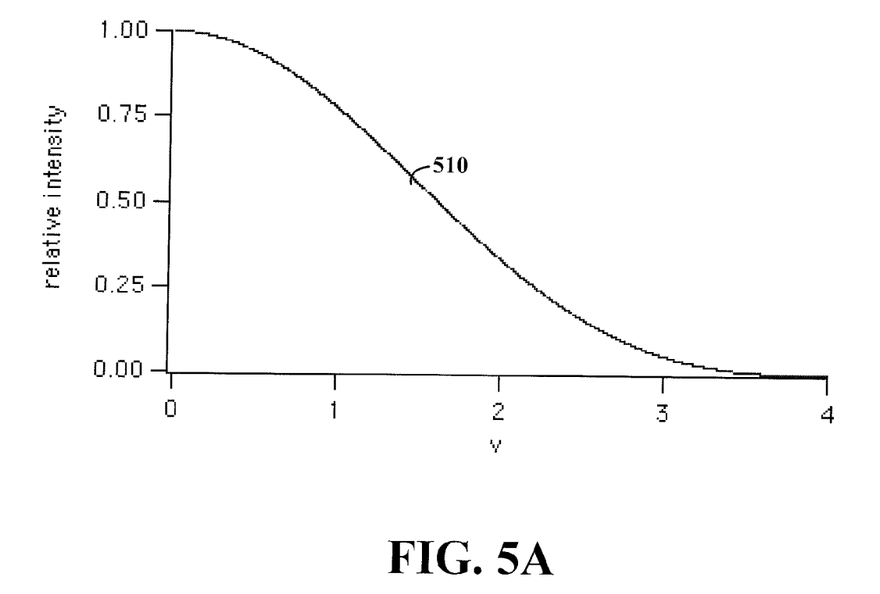
FIGS. 5A and 5B show plots of relative intensities, according other example embodiments of the present invention.
Figure 5B:
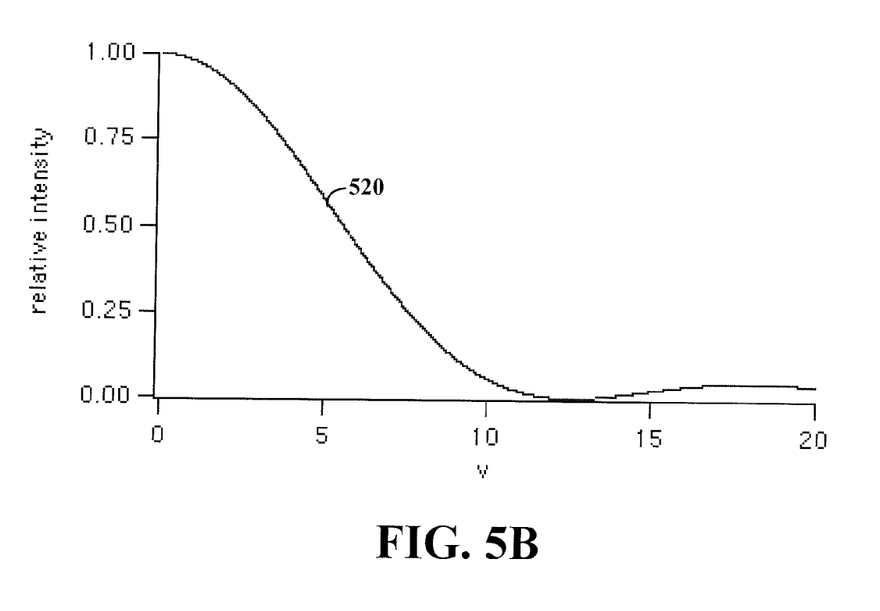

Relative intensities are shown in plots 510 and 520 respectively in FIG. 5A and FIG. 5B.

In two-photon fluorescence, the imaging point spread function is determined by the square of the excitation intensity distribution:

$$I_{2-p}(u, v) = \left| 2 \int_0^1 J_0(v\rho) \exp(iu\rho^2/2) \rho d\rho \right|^4$$

In-focus PSF can be simplified to:

$$I_{lateral}(v) = \left(\frac{2J_1(v)}{v}\right)^4, \text{ and}$$

$$I_{axial}(u) = \left(\frac{\sin(u/4)}{u/4}\right)^4.$$

Figure 6A:
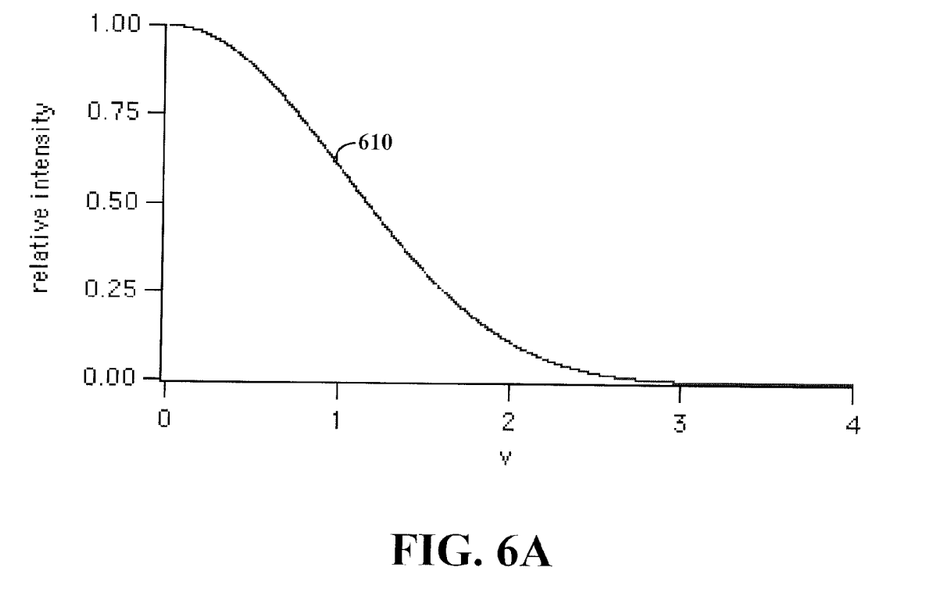
FIG. 6A and FIG. 6B show other plots of relative intensities, according other example embodiments of the present invention.
Figure 6B:
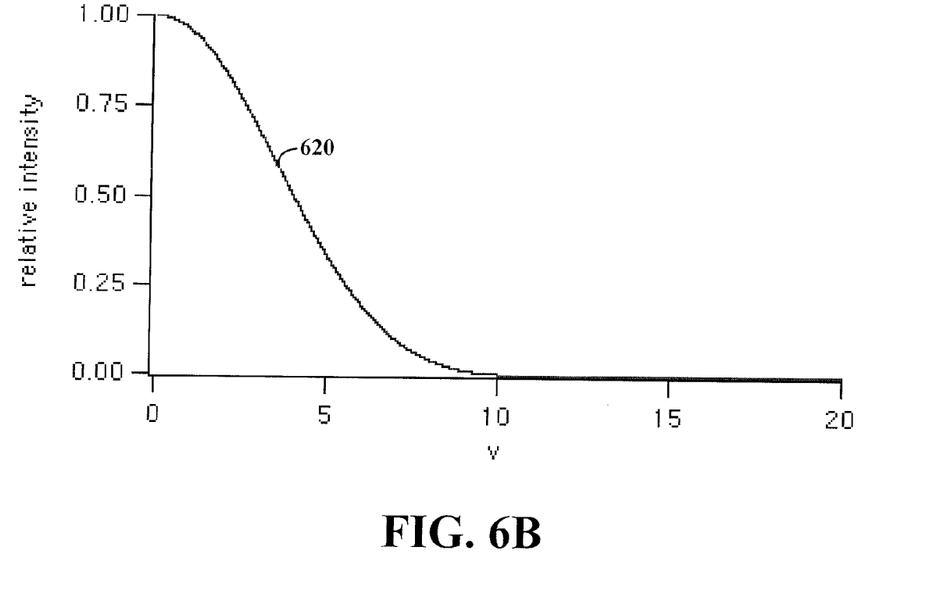

Relative intensities are shown in plots 610 and 620, respectively in FIG. 6A and FIG. 6B.

When comparing the two-photon intensity-squared PSF to the one-photon intensity PSF, the excitation wavelength in two-photon microscopy can be approximately twice the wavelength used for one-photon excitation. For example, for a given wavelength the intensity-squared PSF will be considerably tighter (about 35%) than the intensity PSF. However, in fluorescence microscopy, because the excitation wavelength is doubled for two-photon, one-photon fluorescence will have superior resolution. The resolution of the two-photon microscope relates to relatively robust light scattering compared to one-photon fluorescence. Thus in normal biological samples, two-photon and confocal microscopes are useful for high-resolution applications.

Application to Engelbrecht Microscope

The above experimental embodiments are broadly applicable to many microscope systems. One such system is the Engelbrecht two-photon fiberscope (see, e.g., *Ultra-compact fiber-optic two-photon microscope for functional fluorescence imaging in vivo*, Optics Express, 2008 Apr. 14, which is incorporated herein by reference). The excitation micro-optics include two GRIN lenses of approximate NA 0.2 and 0.5 at 812 nm. The system lateral magnification is 2.5.

Using the 1-photon PSF and the formula for system PSFs, $$FWHM_{1-p, lateral} = 2\frac{1.618}{2\pi}\frac{\lambda}{NA} \approx 0.510\frac{\lambda}{NA}$$

$$\sigma_{system}^2 = \sigma_{endoscope}^2 + \left(\frac{\sigma_{microscope}}{M_{endoscope}}\right)^2$$

A 1-p lateral resolution of about 1.17 micron and axial spot size of about 10.82 micron can be achieved with one or more embodiments. The two-photon resolution is 0.828 micron. In the axial dimension, $$FWHM_{axial} = 2\frac{4.0075}{2\pi}\frac{\lambda n}{4n^2 \sin^2(\alpha/2)} \approx \frac{4n}{\pi}\frac{\lambda}{NA^2}.$$

The two-photon resolution is about 7.77 micron, for certain embodiments.

The various embodiments described herein are provided by way of illustration only and should not be construed to limit the invention. Based on the above discussion and illustrations, including the discussion in the Experimental Embodiments, those skilled in the art will readily recognize that various modifications and changes may be made to the present invention without strictly following the exemplary embodiments and applications illustrated and described herein. For instance, such changes may include using other optics, lenses in addition to GRIN lenses, and arrangements involving GRIN lens correction in other manners such as those involving correction for field curvature and astigmatism. Other changes may involve using a GRIN lens imaging system with compensating optics for one or more of bright-field imaging, confocal fluorescence imaging, multi-photon fluorescence imaging, second harmonic generation (SHG), third harmonic generation (THG), Raman spectroscopy, coherent anti-stokes Raman scattering (CARS), fluorescence lifetime imaging, Forster resonance energy transfer (FRET), fluorescence recovery after photobleaching (FRAP), and types of polarization sensitive imaging. Other applications involve using GRIN-lens compensating optics for improving the resolution and sensitivity of biosensing modalities that do not necessarily generate an image. Such modifications and changes do not depart from the true spirit and scope of the present invention.

What is claimed is:

1. A specimen imaging system comprising:
   a light source;
   a light detector;
   a micro-optical probe including a GRIN lens arrangement to direct light
      from the light source to a specimen, and
      from the specimen to the light detector;
   compensation optics to compensate for aberrations in the GRIN lens arrangement;
   wherein the light detector receives and detects light from the specimen, via the probe, and presents a signal characterizing the detected light as corrected for aberrations via the compensation optics; and
   wherein the compensation optics are arranged to pass source light from the light source to the specimen to compensate for aberrations in the GRIN lens arrangement, wherein light from the specimen is passed via the micro-optical probe to the light detector without passing through the compensation optics.

2. The system of claim 1, further including a dichroic device to direct light from the light source to the micro-optical probe and to direct light from the specimen to the light detector.

3. A specimen imaging system comprising:
   a light source;
   a light detector;
   a micro-optical probe including a GRIN lens arrangement to direct light
      from the light source to a specimen, and
      from the specimen to the light detector;
   compensation optics to compensate for aberrations in the GRIN lens arrangement;
   wherein the light detector receives and detects light from the specimen, via the probe, and presents a signal characterizing the detected light as corrected for aberrations via the compensation optics; and
   further including a dichroic device located between the compensation optics and the specimen, and between the specimen and the light detector, to direct light from the light source passed via the compensation optics to the micro-optical probe, and to direct light from the specimen to the light detector.

4. The system of claim 3, wherein the light source is adapted to direct laser light to the specimen via the micro-optical probe for two-photon microscopy, and wherein the light detector detects light from the specimen in response to the directed laser light.

5. The system of claim 3, wherein the light source is adapted to direct laser light to the specimen via the micro-optical probe for one-photon microscopy, and wherein the light detector detects light from the specimen in response to the directed laser light.

6. The system of claim 3, wherein the GRIN lens arrangement has a diameter of less than about one millimeter, and wherein the micro-optical probe is adapted for insertion into tissue of a specimen for imaging the tissue.

7. The system of claim 3, wherein the compensation optics compensate for aberrations in the GRIN lens arrangement by passing light from the light source to the specimen to facilitate increased light intensity at the focal plane of the micro-optical probe in the specimen.

8. The system of claim 3, wherein
   the compensation optics include a plano-convex lens, and
   the GRIN lens arrangement includes a GRIN rod lens having a refractive index radial profile that compensates for aberrations in the plan-convex lens.

9. The system of claim 3, wherein
   the GRIN lens arrangement includes a GRIN rod lens having a pitch length,
   the GRIN rod lens has a length that is about ¾ of the pitch length, and
   the compensation optics compensate for aberrations in the GRIN rod lens.

* * * * *